United States Patent [19]

Harju et al.

[11] 4,374,756

[45] Feb. 22, 1983

[54] VANADIUM-HYDROGEN-PHOSPHORUS-OXYGEN CATALYTIC MATERIAL

[75] Inventors: Philip H. Harju, Spring Church; Eugene A. Pasek, Export, both of Pa.

[73] Assignee: Koppers Company, Inc., Pittsburgh, Pa.

[21] Appl. No.: 300,710

[22] Filed: Sep. 9, 1981

[51] Int. Cl.³ .............................................. B01J 27/14
[52] U.S. Cl. ..................................... 252/435; 252/437
[58] Field of Search ................................ 252/435, 437

[56] References Cited

U.S. PATENT DOCUMENTS

| | | | |
|---|---|---|---|
| 3,474,041 | 10/1969 | Kerr ................................ | 252/437 X |
| 3,864,280 | 2/1975 | Schneider ......................... | 252/435 |
| 3,888,886 | 6/1975 | Young et al. ..................... | 252/435 X |
| 3,907,707 | 9/1975 | Raffelson et al. ................. | 252/437 |
| 3,975,300 | 8/1976 | Burness ............................ | 252/435 |
| 3,977,998 | 8/1976 | Freerks et al. ................... | 252/435 |
| 4,013,586 | 3/1977 | Dolan et al. ..................... | 252/437 |

FOREIGN PATENT DOCUMENTS 1538031 1/1979 United Kingdom .

OTHER PUBLICATIONS

Selective Oxidation of Butene into Maleic Anhydride K. Zeebot et al. Ukran. Khim., Zhur., vol. 43, 842, (1977).

Primary Examiner—Delbert E. Gantz
Assistant Examiner—William G. Wright
Attorney, Agent, or Firm—Oscar B. Brumback; J. Timothy Keane

[57] ABSTRACT

Catalytic material is provided by a composition comprising the elements vanadium, non-water-contained hydrogen, phosphorus and non-water-contained oxygen. The VHPO elements are present in a relatively fixed atomic ratio range, there being more non-water-contained oxygen present than phosphorus by an atomic ratio of greater than five to one. The catalytic material comprises an anhydrous primary component having vanadium of mixed valence, hydrogen, phosphorus and oxygen in an empirical relationship defined by $VH_xPO_y$, wherein "x" has an average value in a range from about 1.29 to about 1.40, and "y" has an average value in a range from about 5.46 to about 5.55. The anhydrous VHPO catalytic material may also be described by a structural formula $(VO)_m(VO_2)_nH_{2n}(PO_4)_n(P_2O_7)_{m/2}$, wherein $m+n=3$, "m" has an average value in a range from about 0.90 to about 1.07, and "n" has an average value in a range from about 1.93 to about 2.10. The primary component is mostly amorphous and in its substantially anhydrous form is characterized by a powder X-ray diffraction pattern having broad peaks with CuKα d-spacings of 4.30, 4.17 and 3.09 Å. The catalytic material is prepared by a process comprising the steps of reducing vanadium pentoxide with a reducing agent in an aqueous solution of phosphoric acid, followed by the step of oxidizing a portion of the vanadium species with an oxidizing agent to form a slurry of a precipitate containing vanadium(IV) and vanadium(V) in contact with a water solution containing vanadium(IV).

24 Claims, No Drawings

VANADIUM-HYDROGEN-PHOSPHORUS-OXYGEN CATALYTIC MATERIAL

BACKGROUND OF THE INVENTION

There are many catalysts and catalyst preparations known which are useful in the conversion of aromatic or aliphatic hydrocarbon feedstocks to maleic anhydride by partial oxidation with air. Typically used feedstocks are benzene, butane and butenes, for which specific oxidation catalysts have been developed, mostly for fixed-bed catalysis operations. With known catalysts in fixed-bed catalysis operations running at relatively high space velocities (typically at 2500 hr$^{-1}$), maleic anhydride yields of about 75 percent of theory are possible from benzene feedstock, and about 50 percent or less from butane. Typical of these catalysts are catalytic materials comprising a mixture of components selected from compounds of molybdenum, molybdenum oxides, vanadium, vanadium oxides, phosphorus and phosphorus oxides.

In U.S. Pat. No. 3,864,280 to Schneider, for example, there is disclosed a vanadium-phosphorus mixed oxide catalyst for use in oxidation of butane to maleic anhydride, which catalyst is prepared in a non-aqueous medium by reacting hydrogen chloride gas with vanadium pentoxide, followed by reaction with orthophosphoric acid. The Schneider patent discloses as the active ingredient of the catalyst a material designated as the "B-phase", which material is characterized by major X-ray diffraction pattern CuKα d-spacings of 6.3, 4.8, 3.9, 3.13, 2.98 and 2.65 angstroms.

U.S. Pat. No. 3,907,707 to Raffelson et al. discloses phosphorus-vanadium-oxygen catalysts for fluid bed conversion of butane to maleic anhydride, which catalyst is prepared by contacting a pentavalent vanadium compound with a trivalent phosphorus compound in an aqueous medium to form a catalyst precursor containing tetravalent vanadium. The catalyst precursor is heated in air at a temperature of 350° C. to 600° C. until about 20 to 80 atomic percent of the vanadium has been converted to pentavalent vanadium.

U.S. Pat. No. 3,977,998 to Freerks et al. discloses a process for preparing phosphorus-vanadium-oxygen catalysts for use in catalytic oxidation of butane to maleic anhydride wherein a vanadium compound and a phosphorus compound are heated in aqueous solution in the presence of an oxalic acid reducing agent to reduce pentavalent vanadium and then maintain the vanadium species in its tetravalent state. The recovered catalyst precursor material is then calcined at a temperature of 350° C. to 600° C. until 20 to 95 atomic percent of the vanadium has been oxidized to pentavalent vanadium.

British Pat. No. 1,538,031 of Monsanto Company discloses a process for preparing a phosphorus-vanadium-oxygen catalyst useful in catalytic oxidation of butane to maleic anhydride. The catalyst is derived by adding vanadium pentoxide slowly to a refluxing mixture of phosphoric acid and oxalic acid in water, then refluxing the mixture for 72 hours at 97° C., and thereafter evaporating the mixture to dryness overnight at 120° C. Precursor compositions of the catalysts are characterized by either of two X-ray diffraction patterns, one having d-spacings of 7.50, 5.79, 5.25, 4.17, 3.81, 3.63, 3.44, 3.40, 3.08, 2.81, 2.77 or 2.31 Å, and one having d-spacings of 6.70, 5.68, 3.34, 3.16 and 3.09 Å.

Belgian Pat. No. 867,189 of Imperial Chemical Industries Limited discloses a promoted solid oxide composite of vanadium and phosphorus prepared by reacting a vanadium compound with phosphoric acid in an aqueous solution of a strong acid to form a catalyst precursor, followed by evaporating the solution to provide a mixture of compounds including a "B-phase" and a compound having the structure α-VOPO$_4$ as determined by X-ray diffraction. A component present in the dried mixture and characterized as detrimental to the catalyst is described by the structural formula VO(H$_2$PO$_4$)$_2$.

A monograph entitled "Selective Oxidation of Butene into Maleic Anhydride" [K. Zeebot et al., Ukran. Khim. Zhur. 43, 842 (1977)] describes a butene catalyst of the "V/P-mica" group having a composition H$_x$(H$_2$O)$_m$[(V$^{+4}$O)$_x$ (V$^{+5}$O)$_{1-x}$PO$_4$], wherein "x" may have a value of zero to 0.95.

SUMMARY OF THE INVENTION

A composition of matter comprises the elements of vanadium, non-water-contained hydrogen, phosphorus and non-water-contained oxygen, in which composition at least a portion of the non-water-contained oxygen is present in a pyrophosphate functional group. The term "non-water-contained hydrogen" denotes that at least a portion of the hydrogen contained in the composition of matter is present other than as provided by water. The term "non-water-contained oxygen" denotes that at least a portion of the oxygen contained in the composition of matter is present other than as provided by water. Further, at least a portion of this non-water-contained oxygen must be present in the composition of matter as provided by a pyrophosphate radical or chemical group (e.g., tetravalent P$_2$O$_7$); non-water contained oxygen may also be provided by such chemical groups as phosphate (e.g., trivalent PO$_4$) and vanadyl (e.g., divalent VO, and monovalent VO$_2$). The total amount of non-water-contained oxygen in the composition of matter is present in an amount in a ratio of non-water-contained oxygen to phosphorus greater than five to one.

Each of the defined VHPO elements is present relative to another of the VHPO elements within a fixed atomic ratio range to provide material capable of catalytic activity. The phrase "within a fixed atomic ratio range to provide material capable of catalytic activity" indicates that effective catalytic materials are provided in which the relative amounts of the VHPO elements may vary within a defined range for each element relative to another element of the material. It is a characterizing feature of the composition of matter of the invention that the catalytic material contains vanadium of mixed valence, that is, vanadium is present in the material in its +4 and +5 valence states.

The catalytic materials of the invention are definable in various aspects. For example, an improved material capable of catalytic activity, which catalytic material is useful in a process of catalytic oxidation of hydrocarbon feedstock, is provided by a composition of matter comprising a primary component having, in its anhydrous form, vanadium of mixed valence, hydrogen, phosphorus and oxygen in accordance with the empirical formula:

$$VH_xPO_y \qquad (I)$$

wherein "x" has an average value in a range from about 1.29 to about 1.40, and "y" has an average value in a range from about 5.47 to about 5.55.

The anhydrous VHPO primary component of the catalytic material may also be identified by the structural formula:

$$(VO)_m(VO_2)_nH_{2n}(PO_4)_n(P_2O_7)_{m/2} \qquad (II)$$

wherein m+n=3, "m" has an average value in a range from about 0.90 to about 1.07, and "n" has an average value in a range from about 1.93 to about 2.10.

The catalytic material as provided by a composition of matter comprising a primary component having vanadium, hydrogen, phosphorus and oxygen is mostly amorphous and in its anhydrous form is characterized by a powder X-ray diffraction pattern, based on the copper K-shell transition spectrum (CuKα), having major d-spacings of 4.30, 4.17 and 3.09 angstroms.

A material capable of catalytic activity, which material comprises vanadium of mixed valence, hydrogen, phosphorus and oxygen within a fixed atomic ratio range, is prepared by a process comprising the steps of (a) forming a heated mixture of water, phosphoric acid, vanadium pentoxide and a reducing agent to provide a medium for reduction of a portion of vanadium species of +5 valence to vanadium species of +4 valence, and (b) adding to the mixture a non-contaminating oxidizing agent to form a precipitate comprising vanadium of +5 valence and vanadium of +4 valence, whereby there is provided a precipitate, which precipitate provides a precursor to a material capable of catalytic activity. The precipitate may be separated from the water of the mixture so as to obtain a dry-appearing solid material. The dry-appearing solid material may thereafter be heated to provide an anhydrous material having fixed relative amounts of vanadium, hydrogen, phosphorus and oxygen.

The process may be further characterized by a third step of removing free water from the mixture after the reduction-oxidation steps to provide a dry-appearing solid material comprising the precipitate containing vanadium of plus 5 valence and vanadium of plus 4 valence.

The process may be further characterized by a fourth step of heating or calcining the dry-appearing solid material so that the amounts of vanadium, hydrogen, phosphorus and oxygen contained in the material are fixed within catalytically effective ranges of atomic ratio, and so that water of hydration or water of contamination is driven from the material. Generally, heating or calcining of the solid material takes place in a substantially oxygen-free, inert atmosphere.

Catalytic material of the invention is generally useful in the catalytic oxidation of hydrocarbon feedstocks. More particularly, the catalytic material is useful in fluid-bed catalysis in the oxidation of n- butane and benzene feedstock to maleic anhydride. One advantage of fluid-bed catalysis is that relatively high feedstock concentrations may be employed without decreased yields as compared to fixed-bed operations. Hence, catalyst prepared by the method of the invention provides an oxidation process in which relatively high yields of maleic anhydride may be obtained from butane feedstock. Catalyst product made in accordance with the invention has been proved useful in the fluid-bed oxidation of benzene to maleic anhydride. It has been found that freshly prepared catalytic material of the invention has the properties of a "seasoned" catalyst; that is, the catalyst is immediately useful as an oxidation catalyst to provide high conversion rates without time-consuming and costly catalyst break-in or conditioning steps. This advantage is particularly important in fluid bed operations wherein a wide range of break-in conditions are not practical.

DETAILED DESCRIPTION OF THE INVENTION

The term "catalytic activity" connotes the ability of a catalyst to convert a particular hydrocarbon feedstock such as butane to other compounds within a range of specific reaction conditions. The terms "catalytic material", "catalytically effective material" and "material capable of catalytic activity" are intended to denote the same kinds of materials. These materials contain the elements of vanadium, non-water-contained hydrogen, phosphorus and non-water-contained oxygen in amounts relative to each other fixed within a defined atomic ratio range, which relative amounts of VHPO elements are fixed during calcination of the materials. These calcined VHPO materials may be immediately effective as catalysts in hydrocarbon conversion processes. It has been found that if calcined VHPO material takes up water of hydration or becomes water-contaminated, catalytic activity of the material may be reduced. Activity may be restored by removing water of hydration or water of contamination from the material. In describing catalytic material of the invention, the terms "anhydrous" and "substantially devoid of water" are intended to denote VHPO material lacking those amounts of water which significantly reduce the catalytic activity of the VHPO material. These calcined VHPO catalytic materials are distinguishable from a composition of matter of the invention which provides a catalytic material precursor, that is, the composition of matter which is provided by a precipitate formed after the reduction-oxidation steps.

In the reduction step for preparing catalytic material of the invention, it is preferred that a heated mixture be prepared in the form of an aqueous slurry. The slurry is formed by mixing together water, phosphoric acid and vanadium pentoxide having vanadium of +5 valence. Then the mixture is heated and there is added to the mixture an amount of a reducing agent sufficient to form a water solution in contact with the slurry, with the water solution containing vanadium of +4 valence formed by reduction of a portion, but not all, of the vanadium of +5 valence.

Reducing agents suitable for use in the reduction step include practically any compound capable of reducing a portion of the vanadium of +5 valence to vanadium of +4 valence in the presence of phosphoric acid while leaving no residue which substantially retards the catalytic effectiveness of the material. Typically useful reducing agents include oxalic acid, phosphorous acid and glycolic acid.

It is preferred that catalytic material prepared by the process of the invention contain fixed relative amounts of phosphorus and vanadium in an atomic ratio range of phosphorus to vanadium from about 0.85 to one to about 1.15 to one; especially preferred is an atomic ratio range of phosphorus to vanadium from about 0.95 to one to about 1.05 to one. In order that the finally prepared catalyst material contain a P/V atomic ratio in the desired range, the mole ratio of phosphoric acid to vanadium pentoxide introduced initially in the mixture, when a non-phosphorus-containing reducing agent is utilized, preferably should be in a range from about 1.7 to one to about 2.3 to one; a mole ratio range of about 1.9 to one to about 2.1 to one is especially preferred. In preparations utilizing a phosphorus-containing reducing agent, the mole ratio of phosphoric acid to vanadium pentoxide will be adjusted to take into account the presence of the phosphorus in the reducing agent in order to achieve the stated ratios.

The preferred embodiment of the process of the invention entails preparation of a slurry of vanadium pentoxide in a phosphoric acid-and-water solution, with the phosphorus and vanadium present in amounts sufficient to provide an atomic ratio of phosphorus to vanadium in the slurry preferably in a range from about 0.85 to one to about 1.15 to one, and more preferably in the range from about 0.95 to one to about 1.05 to one. Generally, the slurry is heated to a temperature of about 90° C. before the reducing agent, preferably oxalic acid, is added to the slurry. Then the oxalic acid reducing agent is added slowly to the slurry with mixing. A mixture is then formed comprising the slurry in contact with a water solution of oxalic acid. The temperature of the mixture is maintained during reaction of the oxalic acid in the mixture in a range from about 80° C. to about 100° C.

The presence of oxalic acid and phosphoric acid in the mixture of the preferred embodiment provides a moderately acidic aqueous medium in which at least a portion of vanadium of +5 valence furnished by the vanadium pentoxide is reduced to vanadium of +4 valence. The reduced species is soluble in the water solution, while vanadium species of +5 valence comes substantially out of water solution to form a slurry. The proportion of the available vanadium species of +5 valence which is reduced to vanadium of +4 valence depends chiefly upon the mole ratio of oxalic acid to vanadium pentoxide, although the rate of vanadium reduction is dependent upon physical mixing and temperature of the mixture.

It is known that in a hot aqueous solution containing oxalic acid and vanadium pentoxide in a 3 to 1 mole ratio, vanadyl oxalate is formed, as expressed by Equation III:

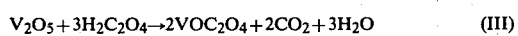

$$V_2O_5 + 3H_2C_2O_4 \rightarrow 2VOC_2O_4 + 2CO_2 + 3H_2O \quad \text{(III)}$$

It is a preferred aspect of the present invention that not necessarily all of the available vanadium species of +5 valence is reduced to vanadium of +4 valence and complexed with oxalate ion. Hence, it is preferred that less than three moles of oxalic acid be used to one mole of vanadium pentoxide, e.g., about one to two moles of oxalic acid. One mole of oxalic acid in theory is sufficient to reduce one mole of vanadium pentoxide to two moles of vanadyl ion species (VO++), provided sufficient H+ species can be supplied from another acid, according to Equation IV:

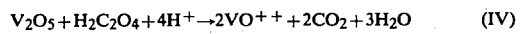

$$V_2O_5 + H_2C_2O_4 + 4H^+ \rightarrow 2VO^{++} + 2CO_2 + 3H_2O \quad \text{(IV)}$$

It has been found, however, that the reaction of equimolar amounts of vanadium pentoxide and oxalic acid as expressed in Equation IV does not go to completion when the H+ species is supplied by phosphoric acid and the mole ratio of phosphoric acid to vanadium pentoxide is about two to one. For reduction of substantially all of the vanadium +5 species to vanadium +4 species, there would be required in the mixture at least a 30 to 50 mole percent excess of oxalic acid beyond the one to one mole ratio of oxalic acid to vanadium pentoxide. Preferably, the amount of oxalic acid present is in a mole ratio of oxalic acid to vanadium pentoxide of about one to one.

In the preferred method of preparing a mixture comprising a slurry, phosphoric acid is firstly dissolved in water. After heating of the phosphoric acid solution to a temperature in a range of 80° to 100° C., preferably at least about 90° C., vanadium pentoxide is added to form a slurry. Then to the slurry there is slowly added oxalic acid. After the addition of the oxalic acid is completed, the temperature of the mixture is maintained in the aforementioned range for a period of time to allow reduction of a portion of the pentavalent vanadium to tetravalent vanadium. The proportion of available vanadium(V) which is reduced to vanadium(IV) is generally a substantial portion, but not all, of the available vanadium(V). Typically, the amount of vanadium(V) reduced to vanadium(IV) is in a range from about 90 atomic percent to less than 100 atomic percent of the total amount of vanadium available for reduction.

After the reduction step, a non-contaminating oxidizing agent is added to the mixture. The term "non-contaminating oxidizing agent" is intended to describe compounds which oxidize a portion of the vanadium species of +4 valence to vanadium species of +5 valence but which contribute no residue that is detrimental to operation of the catalyst. Examples of suitable non-contaminating oxidizing agents are hydrogen peroxide, ozone, oxygen and air. A preferred oxidizing agent is hydrogen peroxide, such as may be furnished by a 30 percent or greater amount of hydrogen peroxide solution in water.

The quantity of an oxidizing agent required to be added to the mixture depends chiefly upon three factors. Firstly, the quantity of oxidizing agent must be roughly proportional to the amount of reducing agent used in preparing the mixture and the quantity must be increased in accordance with the amount of excess reducing agent used. Secondly, the quantity of oxidizing agent required may be made smaller when an increased amount of oxygen is present during calcination of the solid catalyst material to fix the relative amounts of the VHPO elements in the catalyst components. Thirdly, it may be necessary to increase the quantity of oxidizing agent required because of loss of the agent through disproportionation, as occurs increasingly with peroxide compounds, such as hydrogen peroxide, at elevated temperatures. Thus, the quantity of oxidizing required is dependent upon the type of oxidizing agent used and the temperature to which the mixture is cooled before the oxidizing agent is added. Generally, such as for hydrogen peroxide, cooling is required only to an extent to prohibit substantial disproportionation of the oxidizing agent.

All of these factors must be considered in determining the quantity of oxidizing agent to be used, together with reaction conditions such as temperature, the degree and duration of mixture agitation and the type and size of the reaction vessel. Generally, the amount of oxidizing agent used is that amount required to cause oxidation of about 10 to about 70 atomic percent of the vanadium species of plus 4 valence to vanadium species of plus 5 valence. Typically, as in the use of hydrogen peroxide as the oxidizing agent and oxalic acid as the reducing agent, about 0.9 mole of hydrogen peroxide may be used for one mole of oxalic acid used in the reduction step. Usually, the hydrogen peroxide is introduced into the mixture as a 30 percent hydrogen peroxide solution in water. Excessive hydrogen peroxide disproportionation may be avoided by maintaining reaction temperatures below about 40° C., and preferably at a temperature of about 25° C. or less.

Although precise reaction mechanisms are not known, it is believed that during the oxidation step a portion of the amount of oxalate ion which was provided by the oxalic acid reducing agent is oxidized to carbon dioxide and a portion of the vanadium of plus 4 valence is oxidized to vanadium of plus 5 valence. Since these reactions are exothermic, it is desirable that the reaction mixture be held to a temperature not greater than about 40° C. so that disproportionation of the oxidizing agent is minimized.

Upon addition of the oxidizing agent to the mixture, solid material, usually green in color, forms in the solution. The solid material is a precipitate containing vanadium plus 5 and vanadium plus 4 species in an atomic ratio of about two to one, while the supernatant mother-liquor contains vanadium substantially of the plus 4 valence species.

After the oxidation step is completed, the volume of the mixture is reduced by removal of water of solution. In the practical preparation of the catalytic material, there is no need to separate the solid material from the mother-liquor during the water-removal step. It may be convenient, however, in some preparation methods to remove the precipitate from contact with the mother-liquor before removal of the water of solution; the mother-liquor may then be recycled to a batch of the mixture awaiting addition of oxidizing agent. The water may be removed from the mixture in the practical preparation by evaporation, as by heating the mixture to its boiling point. Heating continues until all of the free water is removed from the slurry of the preferred mixture so that a substantially dry-appearing solid material remains containing the precipitate and residue of the supernatant liquid. This solid material which is made up of precipitate and mother-liquor residue contains a complex, intimate mixture of compounds. The precipitate constitutes an intermediate composition of matter which provides a precursor to the catalytic material and to the material capable of catalytic activity. It is believed that compounds derived from the mother-liquor residue are not necessary for optimum effectiveness of the catalytic material of the invention.

The solid material derived from the mixture may be dried by various methods to remove water retained in the solid matter. The solid material may be dried in an oven at about 150° C. at atmospheric pressure until there appears dry, green-colored material. Alternatively, the solid material may be dried at reduced pressure and at lower temperatures or may be spray-dried. When spray-drying is used to remove the water, it may be necessary to provide a binder to the slurry which aids in maintaining a minimum particle size of the dried material.

After drying the solid material, it is necessary to provide controlled heating or calcining of the material in order to drive off substantially all of the remaining water and in order to fix the relative amounts of vanadium, hydrogen, phosphorus and oxygen in the solid material. To some extent during the calcination step, the relative atomic ratios of the VHPO elements may be adjusted by controlling the level of oxygen present in the calcining atmosphere, in a case where an ineffective amount of oxidizing agent was used in the oxidation step. The heating step, which may be characterized as a "calcination" step, is usually carried out in a partially or totally inert atmosphere. For example, calcining of the solid material may take place in a muffle furnace having means for introducing an inert gas, such as nitrogen, into the furnace. The nitrogen displaces atmospheric air and reduces the level of available oxygen in the furnace. Calcination takes place typically in a range of about 375° C. to about 385° C. The duration of heating typically averages from about one to about three hours, with two hours being preferred.

The catalytic material of the invention is preferably utilized in fluid-bed catalysis operations in the oxidation of butane to maleic anhydride. For a fluid-bed operation, a range of particle sizes is desirable. Generally, a useful range of particle sizes is from 20 microns to about 200 microns, with about 95 percent of the particles falling within this range. An assembly of particles within this range may be obtained from a spray-drying step in which appropriate spray-drying equipment is used. Also, useful particle size distributions may be obtained by grinding the calcined solid material in a grinding vessel followed by screening of the ground material and blending to obtain appropriate particle sizes.

Catalytic material may be prepared by the process of the invention which substantially comprises porous particles having a mean pore diameter in a range from about 450 Å to about 1500 Å.

The precipitate formed from the mixture after the reduction-oxidation steps contains a precursor to the VHPO primary component of the catalytic material, which primary component in its anhydrous form is chiefly responsible for the catalytic activity of the material. The primary component is derived from its precursor during the calcination step, which step is carried out in the presence of a substantially inert atmosphere. This primary component is essentially devoid of water and comprises vanadium, phosphorus and non-water-contained-hydrogen-and-oxygen as defined by the empirical relationship:

$$VH_xPO_y \tag{V}$$

wherein "x" has an average value in a range from about 1.29 to about 1.40, and "y" has an average value in a range from about 5.47 to about 5.55. In preferred embodiments of the invention, the average value of "x" in the empirical formula is about 1.33 and the average value of "y" is about 5.50.

The anhydrous VHPO primary component of the catalytic material may also be identified as a mixed phosphate-pyrophosphate as expressed by the structural formula:

$$(VO)_m(VO_2)_nH_{2n}(PO_4)_n(P_2O_7)_{m/2} \tag{VI}$$

wherein m+n=3, "m" has an average value in a range from about 0.90 to about 1.07, and "n" has an average value in a range from about 1.93 to about 2.10. In preferred embodiments of the invention, the average value of "m" in the structural formula is about 1.0, and the average value of "n" is about 2.0, as expressed by the structural formula:

$$(VO)(VO_2)_2H_4(PO_4)_2(P_2O_7)_{0.5} \tag{VII}$$

The VHPO primary component of the catalytic material is mostly amorphous in structure. However, in a substantially anhydrous form, the primary component is characterized by a powder X-ray diffraction pattern (CuKα) having broad peaks with major d-spacings of 4.30, 4.17 and 3.09 Å. The substantially anhydrous primary component is further characterized by the diffraction pattern peaks having relative intensities as set forth in Table I, below:

TABLE I

| X-ray Diffraction Pattern Characteristics for Anhydrous VHPO Primary Component | |
|---|---|
| d-Spacing (Å) (CuKα) | Relative Intensity |
| 4.30 | 12 |
| 4.17 | 100 |
| 3.09 | 35 |

The diffraction data reported herein are derived from samples, prepared in accordance with the described preparation, as analyzed using a Philips Electronic Instruments APD 3500 Automated Powder Diffraction System. Generally, d-spacing data for any one pattern were derived by averaging grouped peaks.

Vanadium is present in the primary component of the catalytic material as vanadium of mixed valence, that is, as vanadium of plus 4 valence and vanadium as plus 5 valence. Generally, the average valence of vanadium ranges from about 4.64 to about 4.70. More typically, the vanadium is present having an average valence of about 4.67.

The solid material formed after the water-removal step contains, in addition to the described precipitate, a residue of the salt components of the water solution. One of these salt components constitutes a precursor to the secondary component identified in the catalytic material. The secondary component is derived from its precursor during the calcination step in a substantially inert atmosphere. This secondary component is not necessary, it is believed, to optimum catalytic activity of the material. The secondary component has vanadium, phosphorus and non-water-contained oxygen defined by the empirical formula:

$$VPO_w \tag{VIII}$$

wherein "w" has an average value in a range from about 4.5 to about 5.0. Generally, the secondary component comprises substantially entirely vanadium of plus 4 valence, in which case "w" is 4.5. In catalytic material having a secondary component with vanadium of plus 4 valence, the anhydrous VPO secondary component has the structural formula:

$$(VO)_2P_2O_7 \tag{IX}$$

The vanadium(IV) VPO secondary component is characterized by a powder X-ray diffraction pattern as reported by E. Bordes and P. Courtine, Journal of Catalysis, 57, 236 (1979).

Some catalytic material prepared by the process of the invention may also contain an anhydrous VPO tertiary component having vanadium of plus 5 valence such that "w" equals 5.0 in formula VIII. The vanadium(V) tertiary component may be characterized by the structural formula:

$$\alpha\text{-}VPO_4 \tag{X}$$

The X-ray diffraction pattern characteristic of the vanadium(V) VPO tertiary component of formula X has been published by B. Jordan and C. Calvo, Can. J. Chem., 51, 2621 (1973).

The catalyst may also contain small amounts of other vanadium or phosphorus tertiary components conveniently expressed as $V_2O_5$ or $P_2O_5$.

Of course, catalytic material of the invention may comprise the secondary component, or secondary and tertiary components, in addition to the primary component.

A catalyst containing secondary and tertiary components in addition to the primary component has wider ratio ranges of the VHPO elements. For example, the ratio of phosphorus to vanadium may range from about 0.85 to one to about 1.15 to one, with a range of about 0.95 to one to about 1.05 to one being preferred. The ratio of non-water-contained hydrogen to vanadium may range from about 0.6 to one to about 1.3 to one. The ratio of non-water-contained oxygen to phosphorus may range from about 4.6 to one to about 6.1 to one.

For a catalytic material provided by a composition of matter having both primary and secondary components, the components are usually present in amounts as expressed by the formula:

$$a(VH_xPO_y) + b(VPO_w) \tag{XI}$$

wherein $a+b=1$, and "a" may be any value in a range from about 0.5 to 1.0. In a typical sample of catalytic material having both components in accordance with empirical formula XI, the value of "a" may be any value in a range from about 0.75 to 1.0.

The relative amounts of primary and secondary components contained in the catalytic material may be expressed by the ratio of the amount of secondary component of formula VIII to the amount of primary component of formula VI, which ratio may be in a range as expressed in equation XII:

$$0 \leq \frac{VPO_w}{(VO)_m(VO_2)_nH_{2n}(PO_4)_n(P_2O_7)_{\frac{m}{2}}} \leq \frac{t}{1} \tag{XII}$$

wherein generally "t" is about 1.0; preferably, "t" is about 0.33.

In catalytic material as provided by a composition of matter comprising a primary component and a secondary component, as expressed by empirical formula XI, vanadium is present in both of the plus 4 and plus 5 valence states. Generally, in the two-component catalytic material, the total vanadium present has an average valence in a range from about 4.3 to about 4.7; more typically, the total vanadium present has an average valence in a range from about 4.5 to about 4.7.

Freshly prepared catalytic material of the invention is substantially devoid of water of hydration and water of contamination and may be used in a butane catalytic oxidation process to produce maleic anhydride at high yields without the need for lengthy catalyst "break-in" or "conditioning" time. The primary component of the catalytic material is hygroscopic, however, and quickly absorbs water when the component is exposed to ambient atmospheric conditions. It has been found that the presence of water of hydration diminishes the catalytic activity of the material. The catalytic activity of the material may be restored, however, by driving off the water of hydration or contamination, such as by heating the material.

The primary component of the catalytic material may contain various amounts of water of hydration. Thus the primary component of empirical formula V may have water of hydration in accordance with the empirical formula:

$$VH_xPO_y \cdot uH_2O \qquad (XIII)$$

wherein "x" and "y" have values as described, and "u" has an average value of at least about 0.01. More typically, the amount of water of hydration contained in the primary component is that amount present where "u" has an average value in a range from about 0.01 to about 2.0.

The amount of water of hydration of the primary component in structural terms may be expressed as:

$$(VO)_m(VO_2)_nH_{2n}(PO_4)_n(P_2O_7)_{m/2} \cdot uH_2O \qquad (XIV)$$

wherein "m" and "n" have values as described, and "u" has an average value of at least about 0.01. In a typical sample, "u" may have an average value in a range from about 0.01 to about 2.0.

In its hydrated form, the mostly amorphous VHPO primary component is characterized by a CuKα powder X-ray diffraction pattern having broad peaks with d-spacings of 7.17, 6.96, 3.04 and 2.37 Å. The hydrated primary component may be further characterized by the diffraction pattern peaks having relative intensities as set forth in Table II, below:

TABLE II

| X-ray Diffraction Pattern Characteristics for Hydrated VHPO Component | |
|---|---|
| d-Spacing (Å) (CuKα) | Relative Intensity |
| 7.17 | 100 |
| 6.96 | 12 |
| 3.04 | 25 |
| 2.37 | 5 |

It has been observed that the diffraction pattern for the catalytic material changes gradually in accordance with the degree of hydration of the material. For example, as the amount of water taken up by the catalytic material increases, the intensity of the 4.17 Å d-spacing peak can be observed to decrease gradually while the intensity of the 6.96 and 7.17 Å peaks increase. The behavior is attributed to the catalytic material having a layer-like structure, between the layers of which water may be "trapped" so as to expand the layer-like structure.

The secondary component of the catalytic material in its anhydrous form may take up water of hydration and then react with the water in accordance with the following sequence of equations:

$$(VO)_2P_2O_7 + H_2O \longrightarrow 2VOHPO_4 \qquad (XV)$$

$$VOHPO_4 + uH_2O \longrightarrow VOHPO_4 \cdot uH_2O$$

wherein "u" may have an average value of at least about 0.01. Although the catalytic activity of the material is believed to be chiefly attributable to the presence of the VHPO primary component, the presence in moderate quantities of the VPO secondary component or of its various hydrated forms is not deemed to be detrimental to the performance of the catalytic material. A tertiary component, α-VOPO₄, may also become hydrated according to the formula α-VOPO₄·2H₂O.

A theoretical model has been formulated which describes catalytic material of the invention. The model is based on the catalytic material being comprised chiefly of a vanadium(IV) and vanadium(V) VHPO primary component as expressed by structural formula VII, and a vanadium(IV) VPO secondary component as expressed by structural formula IX. Set forth in Table III are the analytical results for ten samples of freshly calcined catalytic material prepared using oxalic acid as the reducing agent. The relative amounts of phosphorus and vanadium in catalyst samples, determined by X-ray flourescence methods, are expressed as phosphorus to vanadium (P/V) atomic ratios. To determine the amounts of vanadium species of +4 valence in the catalyst material, an acidic solution is prepared, preferably from sulfuric acid, which solution contains the two vanadium species. The amount of vanadium of +4 valence in the acid solution is determined by potentiometric titration with either ceric ion of +4 valence or permaganate ion. The amount of vanadium of +5 valence in the acidic solution is then determined by firstly reducing the vanadium of +5 valence with bisulfite, then boiling the solution to remove excess sulfur dioxide, and thereafter retitrating to find the total amount of vanadium in the solution. The amount of vanadium of +5 valence is determined as the difference between the total amount of vanadium present and the firstly titrated amount of vanadium of +4 valence. Theoretical quantities of the primary and secondary components are computed, respectively, from the experimentally determined values of vanadium species of +4 valence and vanadium species of +5 valence. Where the phosphorus-to-vanadium atomic ratios differ from one to one, excess phosphorus in the sample is calculated as phosphorus pentoxide and excess vanadium present in the sample is calculated as vanadium pentoxide.

TABLE III

| | Experimental Verification of VHPO-VPO Model of Freshly Calcined Catalytic Material | | | | | | |
|---|---|---|---|---|---|---|---|
| | Experimental | | | Calculated from Experimental* | | | |
| Sample No. | P/V Mole Ratio | V+4 (wt %) | V+5 (wt %) | 1° (wt %) | 2° (wt %) | P₂O₅ (wt %) | V₂O₅ (wt %) | Total Calc. (wt %) |
| 1 | 0.99 | 10.6 | 19.5 | 96.9 | 3.0 | 0 | 0.5 | 100.4 |
| 2 | 1.00 | 13.2 | 17.8 | 89.8 | 13.0 | 0 | 0 | 102.8 |
| 3 | 0.99 | 15.0 | 15.9 | 78.8 | 21.7 | 0 | 0.5 | 101.0 |
| 4 | 1.00 | 15.0 | 15.3 | 77.2 | 22.2 | 0 | 0 | 99.4 |
| 5 | 1.01 | 14.9 | 14.6 | 73.6 | 23.0 | 0.5 | 0 | 97.1 |
| 6 | 1.05 | 15.9 | 14.4 | 72.6 | 26.3 | 2.1 | 0 | 101.0 |
| 7 | 1.03 | 15.8 | 14.4 | 72.6 | 26.0 | 1.1 | 0 | 99.7 |
| 8 | 1.06 | 17.2 | 13.0 | 65.6 | 32.3 | 2.5 | 0 | 100.4 |

TABLE III-continued

Experimental Verification
of VHPO-VPO Model of Freshly Calcined Catalytic Material

| Sample No. | P/V Mole Ratio | Experimental | | Calculated from Experimental* | | | | Total Calc. (wt %) |
|---|---|---|---|---|---|---|---|---|
| | | $V^{+4}$ (wt %) | $V^{+5}$ (wt %) | 1° (wt %) | 2° (wt %) | $P_2O_5$ (wt %) | $V_2O_5$ (wt %) | |
| 9  | 1.00 | 17.5 | 12.8 | 64.5 | 33.5 | 0 | 0   | 98.0  |
| 10 | 0.90 | 19.2 | 13.6 | 51.6 | 42.5 | 0 | 6.0 | 100.1 |

Ave. = 100.0 wt. %
Dev. = 1.6 wt. %
*1° = Primary Component - $(VO)(VO_2)_2H_4(PO_4)_2(P_2O_7)_{0.5}$
2° = Secondary Component - $(VO)_2P_2O_7$ The experimental data set forth in Table III fully support the theoretical model. For example, the average weight percent for the proposed components of the system total to 100.0 percent for ten samples, there being a standard deviation among the samples of 1.6 percent. Highly significant is the trend of improved catalytic activity of the material in the presence of increased amounts of the VHPO primary component. Samples 1-10 are listed in decending order for the amounts of VHPO primary component in the catalytic material, and in generally ascending order for the amounts of VPO secondary component. Conversion of butane to maleic anhydride in a fluid-bed reactor with 2.5 mole percent butane feed at a 15-second catalyst contact time, using the catalytic material of samples 1-10 prepared in accordance with the aforementioned procedures, provided excellent yields. Catalytic material samples 1-4, having the greater proportions of primary component over secondary component, provided yields of over 90 pounds of maleic anhydride per 100 pounds of butane feedstock, while samples 5-10, having the lesser proportions of the primary component as compared to samples 1-4, provided yields of less than 90 pounds of maleic anhydride.

Fluid-bed catalysts are usually porous, as are the catalysts described herein. It is believed that for catalytic materials of the invention for use in fluid-bed oxidation of butane to maleic anhydride a physical parameter useful for describing catalyst efficacy is mean pore diameter (m.p.d.), as defined in Equation XVI:

$$m.p.d. = \frac{4 \times 10^4 \times (\text{pore volume in cc/g})}{\text{Surface Area in m}^2/\text{g}} \quad (XVI)$$

It has been found that catalysts having mean pore diameters greater than several hundred angstroms provide especially good catalysis properties. The catalysts listed in Table III are considered to have good to excellent catalysis properties and have mean pore diameters in the range from about 450 Å to about 1500 Å. Pore volumes of the catalyst materials range from about 0.12 to about 0.35 cubic centimeters per gram, with an average value being 0.2 cc/g. Measured standard fluid densities of the catalysts averaged 43.5 pounds per cubic foot and ranged from about 38 to about 52 p.c.f. as measured at 300° C. in a one and one-half inch diameter tube at a linear velocity of air of 0.1 ft./sec.

It is a feature of the invention that catalytic materials freshly prepared according to the steps set forth herein are immediately useful as oxidation catalysts. The catalytic materials may thus be characterized as "seasoned catalysts" inasmuch as no lengthy break-in or conditioning period of the catalyst material in its working environment is required. Hence, fairly high yields of maleic anhydride are attainable immediately.

It is another feature of the invention that in a process for partial oxidation of a hydrocarbon utilizing catalytic material having a high content of primary component, low reactor temperatures, e.g., in the range of about 360° C. to about 380° C., can be used without the presence of a promoter in the catalytic material to increase activity.

As used in the working examples herein, the term "yield" is defined as pounds of maleic anhydride produced per 100 pounds of hydrocarbon feed introduced into the reaction zone. The term "contact time" refers to the length of time the total feed is in contact with the fluidized catalytic material, and may be defined as the volume of the reactor occupied by the catalyst (i.e., catalyst bed height times the cross-sectional area of the reactor), divided by the total feed in volume units per second, measured at 375° C. and 15.4 psia. For example, after charging a reactor with the catalyst material and raising of the reactor temperature to above 340° C., butane feed may be applied at a concentration of about 1.5 to about 4.0 mole percent butane-in-air with a catalyst average contact time of about 5 to about 25 seconds. Typically, a butane-in-air feed concentration of about 2.5 mole percent is utilized with a catalyst contact time of about 15 seconds. Initial yields in excess of 70 pounds maleic anhydride product per 100 pounds of butane feed are obtainable within two hours of catalyst operation. Typically, a 70 percent conversion of the feed to product occurs initially at a reactor temperature of about 380° C. or less., although reactor temperatures in a range of about 350° C. to about 400° C. may be used with good yields. Higher temperatures may be used to increase conversion efficiency to 90 to 95 percent. It has been found that catalytic materials of the invention provide consistent conversion efficiencies ranging from 85 to 92 percent at 2.5 mole percent butane-in-air feed with a 15 to 20 second contact time.

As with most catalyst systems, steady-state operation of the catalyst material is not usually achieved initially. Though fairly high yields are achievable upon initial use of the catalyst, yields are observed to increase over at least the first 24-hour period of catalyst use. Also, the catalytic material provides an increase in product yield with increasing catalyst-to-feed residence or contact time. Commercially available reactors, used with these exothermic reactions and relatively high material throughput rates, are most conveniently designed for contact times of 10 to 30 seconds. The catalytic materials of the invention are useful for yield improvements in other fluid-bed catalysis operations. It is believed that the relative ease of preparation of catalytic material of the invention, which substantially reduces catalyst cost, offsets the relatively higher catalyst contact time which may be necessary for some conversion processes.

The following examples set forth specific embodiments of the invention. The invention is not, however, to be construed as being limited to these embodiments for there are numerous possible variations and modifications. All parts and percentages recited in the examples and throughout the specification are by weight, unless otherwise specified.

EXAMPLE I

To a reaction vessel equipped with heating and stirring means, there was charged 406.3 ml. of a solution of 85.4 percent by weight-in-water phosphoric acid together with 2.0 liters of water. The mixture was heated to a temperature of about 90° C. and then maintained at a temperature of 80° to 90° C. during the addition, with mixing, of 545.7 grams vanadium pentoxide and 756 grams of oxalic acid monohydrate over a 40-minute period. The temperature of the mixture was then maintained at 80° to 90° C. for an additional 1.5 hours, at the end of which time a dark blue solution was obtained. To the heated mixture there was then slowly added 800 ml. of a solution of 30 percent hydrogen peroxide in water. Near the end of the addition period, solid material was observed to appear in the solution. The mixture was placed in an oven maintained at a temperature of about 155° C. to evaporate substantially all the free water from the mixture. The dry-appearing solid material was then placed in a substantially inert atmosphere within a muffle furnace maintained at about 380° C. for a period of about two hours. The solid material was ground and screened for use as a fluid-bed catalyst. Analysis of the catalyst utilizing the aforementioned procedures showed that the catalyst material comprised 22.2 percent secondary component and 77.2 percent primary component. The catalytic material was characterized in having a pore volume of 0.27 cc/g, a mean pore diameter of 650 Å and comprised particles of sizes in accordance with the following distribution:

| Tyler Mesh Size Fraction | Wt. % Present |
| --- | --- |
| +140 | 23 |
| 140–200 | 30 |
| 200–325 | 30 |
| −325 | 17 |

To a laboratory-type reactor having a one and one-half inch diameter, there was charged 219 grams of the previously prepared catalyst. The charged reactor was measured as having a standard fluidized density of 46.9 pounds per cubic foot. The reactor was heated to about 340° C. with an air flow rate established to give a catalyst contact time of 15 seconds. Butane feedstock (99% pure) was supplied to the reactor at a concentration of 2.5 mole percent in air and the temperature was observed to increase to about 380° C. Within two hours of initial operation of the catalyst material, a conversion efficiency of 80 percent was obtained. After 75 hours the yields, per 100 pounds of butane at a 2.5 mole percent feed rate, were 96 pounds for a 20-second contact time and 90.5 pounds maleic anhydride for a 15-second contact time. For the 15- and 20-second contact times, respectively, temperatures for operation were observed to be at 370° C. and 360° C. with conversion efficiencies being, respectively, 85 percent and 86.5 percent.

EXAMPLE II

A reactor equipped with heating and stirring means was charged with 412.8 ml. of a solution of 85.4 percent by weight-in-water phosphoric acid together with 1.5 liters water. The mixture was heated to about 80° C., and over a 15-minute period, there was added to the reactor 545.7 grams vanadium pentoxide and 378 grams oxalic acid dihydrate. The mixture was maintained at a temperature of 80° C. to 90° C. for about 1.5 hours, after which time a bluish-green slurry was formed. The mixture was cooled to about 25° C. and then 200 ml. of a solution of 30 percent hydrogen peroxide-in-water was added to the mixture over a 40-minute period. The temperature of the mixture was observed to increase to about 44° C. The mixture was then heated to about 60° C., with stirring, and thereafter placed in an oven maintained at a temperature of about 150° C. to remove substantially all of the free water in the mixture. The dry-appearing solid material was then placed in a muffle furnace and heated to a temperature of 380° C. within a substantially inert atmosphere for about two hours. The solid material, green in color, was ground and screened. The catalytic material was characterized in having a pore volume of 0.22 cc/g, a mean pore diameter of 850 Å and comprised particles of sizes in accordance with the following distribution:

| Tyler Mesh Size Fraction | Wt. % Present |
| --- | --- |
| +140 | 21 |
| 140–200 | 29 |
| 200–325 | 29 |
| −325 | 21 |

To a laboratory-type reactor having a one and one-half inch diameter, there was charged 206 grams of the previously prepared catalyst material. The charged reactor was measured as having a standard fluidized density of 48.6 pounds per cubic foot. The reactor was heated to a temperature of about 340° C. with an air flow rate established to give a catalyst contact time of about 15 seconds. Butane feedstock (99% pure) was supplied to the reactor at a concentration of 2.5 mole percent butane-in-air. An initial conversion efficiency of 74 percent was obtained at 370° C. After 100 hours of the reactor operation, a conversion efficiency of 85 percent at 383° C. was obtained for a contact time of 20 seconds, with a yield of 102 pounds maleic anhydride per 100 pounds butane at a 2.5 mole percent butane feed.

EXAMPLE III

To a reaction vessel equipped with heating and stirring means, there was charged 2836 ml. of a solution of 85.4 percent by weight-in-water phosphoric acid together with 10.5 liters water. The mixture was then treated according to the procedures of Example II, there having been added 3820 grams vanadium pentoxide, 2646 grams oxalic acid dihydrate and 1.4 liters of 30 percent hydrogen peroxide-in-water.

After the catalyst material was dried to remove free water by evaporation, the catalyst material was divided into two approximately equal lots for calcination. Lot A was placed in a muffle furnace and calcined at a temperature of about 385° C. for two hours in a substantially inert atmosphere. Lot B was placed in a muffle furnace and calcined at a temperature of about 380° C. for two hours in a substantially inert atmosphere. Relative amounts of the primary and secondary components measured in Lots A and B are as follow:

| Component | Lot A | Lot B |
|---|---|---|
| Primary | 96.9 wt. % | 78.8 wt. % |
| Secondary | 3.0 wt. % | 21.7 wt. % |

Catalyst materials from Lot A and Lot B were conditioned separately and then combined in approximately equal proportions. To a laboratory-type reactor described as in Example II, there was charged 207 grams of the catalyst from the combined lots. After 208 hours on-stream, a conversion efficiency of 89.5 percent was obtained at a reactor temperature of 383° C. at 2.5 mole percent butane-in-air feed (using 99% pure butane component) and at a contact time of about 20 seconds, with a yield of 101 pounds maleic anhydride per 100 pounds butane. At higher concentrations of feed at a contact time of 20 seconds, yields were obtained, per 100 pounds butane feed, of 90 pounds maleic anhydride at 3.3 mole percent butane feed and 86 pounds maleic anhydride at 4.0 mole percent butane feed, those yields amounting to conversions of 82.5 percent and 81 percent, respectively.

After 210 hours on-stream with butane, the feed was switched to nitration-grade benzene. A benzene-in-air feed mixture at 3.0 mole percent concentration was introduced into the reactor. Reaction parameters and results are summarized as follow:

| Yield Lbs. MAA | Benzene Conversion Wt. % | Reactor Temp. °C. | Contact Time Seconds |
|---|---|---|---|
| 64.5 | 87 | 425 | 13.3 |
| 66.0 | 89 | 416 | 18.6 |
| 69.5 | 92 | 403 | 22.5 |

After 69 hours on-stream with benzene, the feed was switched back to butane. At 2.5 mole percent butane-in-air and at a contact time of 20 seconds, the maleic anhydride yield was 100 pounds at a temperature of 380° C. with a conversion of 87 percent.

EXAMPLE IV

A reactor equipped with heating and stirring means was charged with 1.5 liters of water and 412.8 ml. of 85.4 percent by weight-in-water phosphoric acid. The mixture was heated to about 80° C., and over a 15-minute period, 545.7 grams vanadium pentoxide and 378.0 grams of oxalic acid dihydrate were added in incremental amounts. The mixture was heated at about 80° C. for about 90 minutes. The mixture which contained a slurry in contact with a water solution was cooled to about 25° C., and then 200 ml. of a water solution of 30 weight percent hydrogen peroxide was added dropwise over a 40-minute period. Temperature of the mixture was observed to rise to a maximum of 46° C. The mixture was further heated to about 60° C., with stirring, and then heated to dryness at about 150° C. The dried solid material was calcined at about 380° C. for two hours in a substantially inert atmosphere. Resulting green solid material was ground and screened to make a fluid-bed catalyst powder. Analysis of the solid material showed the presence of the primary and secondary components as 64.5 and 33.5 weight percent, respectively. The catalytic material was characterized in having a pore volume of 0.21 cc/g, a mean pore diameter of 820 Å and comprised particles of sizes in accordance with the following distribution:

| Tyler Mesh Size Fraction | Wt. % Present |
|---|---|
| +140 | 19 |
| 140–200 | 31 |
| 200–325 | 33 |
| −325 | 17 |

To a laboratory reactor as described in Example I, there was charged 181 grams of the catalyst powder. The fluidized density was measured as 40.5 pounds per cubic foot. After a pre-heating period with air at 340° C., the initial conversion efficiency of butane to maleic anhydride was 52 percent at 382° C. After 180 hours the yield was observed to be 88 pounds of maleic anhydride at a 19-second contact time and a 2.5 mole percent butane-in-air feed (using 99% pure butane component), with a conversion efficiency of 85 percent at 415° C.

EXAMPLE V

A reaction vessel, equipped with heating and stirring means and a reflux condenser, was charged with three liters of water, 255.0 grams of 97.7 percent by weight-in-water phosphorous acid, and 229.4 ml. of 85.4 percent by weight-in-water phosphoric acid. Then 545.7 grams of vanadium pentoxide was added to the solution with stirring to form a mixture having a slurry in contact with the water solution. The mixture was heated under reflux conditions for about 20 hours. The water solution, appearing dark blue in color, was cooled to about 25° C. and then 150 ml. of 30 percent by weight-in-water hydrogen peroxide was added while the temperature of the mixture was maintained below 40° C. The resulting green slurry was dried at about 155° C. to remove substantially all free water from the mixture. The green solid material was calcined at about 380° C. in a substantially inert atmosphere for about two hours. The material was then ground, screened and blended to provide a catalytic material for use in a fluid bed catalysis reactor. Analysis of the catalytic material showed that the material comprised 55.0 percent of the primary component and 39.4 percent of the secondary component. The catalytic material was characterized in having a pore volume of 0.19 cc/g, a mean pore diameter of 1200 Å and comprised particles of sizes in accordance with the following distribution:

| Tyler Mesh Size Fraction | Wt. % Present |
|---|---|
| +140 | 16 |
| 140–200 | 25 |
| 200–325 | 43 |
| −325 | 16 |

To a laboratory reactor as described in Example I, there was charged 197 grams of the catalytic material. A standard fluidized density of 44.7 pounds per cubic foot was measured for the charged reactor. An initial conversion efficiency was measured as 72 percent at 440° C. After 34 hours a conversion efficiency of about 79 percent at 435° C. was obtained for a 20-second contact time, with a yield of 81 pounds of maleic anhydride per 100 pounds of butane at a 2.5 mole percent butane-in-air feed (using 99% pure butane component).

EXAMPLE VI

A reaction vessel, equipped with heating and stirring means and a reflux condenser, was charged with 60 liters water, 4.96 kilograms of 99.2 percent by weight phosphorous acid, and 4.0 liters of 85.4 percent by weight-in-water phosphoric acid. Then 10.91 kilograms of vanadium pentoxide was added to the solution with stirring to form a mixture having a slurry in contact with the water solution. The mixture was heated under reflux conditions for about 22 hours. The water solution, appearing dark blue in color, was cooled to about 25° C. and then 3.46 kilograms of 30 percent by weight-in-water hydrogen peroxide was added to the mixture while the temperature was maintained below 40° C. The resulting green slurry was dried in a vacuum oven to remove substantially all free water. The green solid material was placed in a muffle furnace and calcined at about 380° C. for about two hours in a substantially inert atmosphere. The solid material was ground and sized to provide a catalytic material for use in a fluid bed catalysis reactor. Analysis of the catalytic material showed that the material comprised 85.2 percent of the primary component and 17.1 percent of the secondary component. The catalytic material was characterized in having a pore volume of 0.21 cc/g, a mean pore diameter of 690 Å and comprised particles of sizes in accordance with the following distribution:

| Tyler Mesh Size Fraction | Wt. % Present |
|---|---|
| +140 | 16 |
| 140–200 | 33 |
| 200–325 | 33 |
| −325 | 18 |

About 253 grams of the catalytic material was charged to a laboratory reactor as previously described in Example I. A standard fluidized density of 49.2 pounds per cubic foot was measured for the charged reactor. An initial conversion efficiency of 74 percent was obtained at 380° C. After 75 hours a conversion efficiency of 82.5 percent at 390° C. was obtained for a contact time of 15 seconds, with a yield of 92 pounds of maleic anhydride per 100 pounds of butane at 2.5 mole percent butane-in-air feed (using 99% pure butane component).

EXAMPLE VII

A reactor vessel, equipped with heating and stirring means and a reflux condenser, was charged with three liters of water, 255.0 grams of 97.7 percent by weight phosphorous acid, and 209.4 ml. of 85.4 percent by weight-in-water phosphoric acid. Then 545.7 grams of vanadium pentoxide was added to the solution with stirring to form a mixture having a slurry in contact with the water solution. The mixture was heated under reflux conditions for about 20 hours. The water solution, appearing dark blue in color, was cooled to about 25° C. and then 326 grams of 30 percent by weight-in-water hydrogen peroxide was added while the temperature of the mixture was maintained below 40° C. The resulting green slurry was dried at about 150° C. to remove substantially all free water from the mixture. The green solid material was calcined at about 380° C. in a substantially inert atmosphere for about two hours.

The material was then ground, screened and blended to provide a catalytic material for use in a fluid bed catalysis reactor. The catalytic material was characterized in having a pore volume of 0.18 cc/g, a mean pore diameter of 730 Å and comprised particles of sizes in accordance with the following distribution:

| Tyler Mesh Size Fraction | Wt. % Present |
|---|---|
| +140 | 17 |
| 140–200 | 28 |
| 200–325 | 41 |
| −325 | 14 |

To a laboratory reactor as described in Example I, there was charged an amount of catalytic material, prepared above, sufficient to provide a fluidized bed height of 9.6 inches. A standard fluidized density of 53.3 pounds per cubic foot was measured for the charged reactor. The reactor was operated for a period of 1100 hours at a 2.5 mole percent butane-in-air feed (using 99 percent pure butane component) and at a 15 second contact time. As shown in the following tabulation, the yield of maleic anhydride remained essentially constant during the test period.

| Yield (lbs MAA/100 lbs butane) | Conv., Wt. % | Temp. °C. | Hours |
|---|---|---|---|
| 86 | 82.5 | 415 | Initial |
| 84.5 | 80.5 | 395 | |
| 85.5 | 78.5 | 397 | |
| 85 | 78 | 395 | |
| 86 | 79.5 | 400 | |
| 86 | 80.5 | 402 | 1100 |

Although specific examples of the instant invention have been set forth hereinabove, it is not intended that the invention be limited solely thereto, but is to include all the variations and modifications falling within the scope of the appended claims.

What is claimed is:

1. Catalyst for partial oxidation of hydrocarbons, said catalyst comprising vanadium, non-water-contained hydrogen, phosphorus and non-water-contained oxygen, said vanadium present as a mixture of vanadium of plus 4 valence and vanadium of plus 5 valence, and at least a portion of said phosphorus and said non-water-contained oxygen present in a pyrophosphate group.

2. The catalyst of claim 1 wherein the atomic ratio of phosphorus to vanadium is in a range from about 0.85 to one to about 1.15 to one.

3. The catalyst of claim 1 wherein the atomic ratio of phosphorus to vanadium is in a range from about 0.95 to one to about 1.05 to one.

4. The catalyst of claim 1 wherein the atomic ratio of non-water-contained hydrogen to vanadium is in a range from about 0.6 to one to about 1.4 to one.

5. The catalyst of claim 1 wherein the atomic ratio of non-water-contained oxygen to phosphorus is in a range from about 4.6 to one to about 6.1 to one.

6. The catalyst of claim 1 wherein vanadium is present as a mixture of vanadium of plus 4 valence and vanadium of plus 5 valence, said mixture of vanadium having an average valence in a range from about 4.3 to about 4.7.

7. The catalyst of claim 1 further comprising water of hydration.

8. A composition of matter comprising a first component substantially devoid of water and having vanadium, non-water contained hydrogen, phosphorus and non-water contained oxygen in accordance with the empirical formula:

$$VH_xPO_y$$

wherein "x" has a value in a range from about 1.29 to about 1.40, and "y" has a value in a range from about 5.47 to about 5.55, at least a portion of said non-water contained oxygen present in a pyrophosphate group.

9. The composition of matter of claim 8 wherein said vanadium is present as vanadium of plus 4 valence and vanadium of plus 5 valence.

10. The composition of matter of claim 8 wherein said vanadium has an average valence in a range from about 4.64 to about 4.70.

11. The composition of matter of claim 8 further comprising a second component substantially devoid of water and having vanadium, phosphorus and oxygen in accordance with the empirical formula:

$$VPO_w$$

wherein "w" has an average value of about 4.5; said first component and said second component being present in said composition in the following proportional amounts:

$$a(VH_xPO_y)+b(VPO_w)$$

wherein a+b=1, and "a" has a value in a range from about 0.5 to 1.0.

12. The composition of matter of claim 11 further comprising additional components provided by oxides of vanadium, oxides of phosphorus, or vanadium-phosphorus oxides, such that the phosphorus to vanadium ratio of said composition of matter is in a range from about 0.85 to one to about 1.15 to one.

13. The composition of matter of claim 12 wherein the total vanadium of said components has an average valence in a range from about 4.3 to about 4.7.

14. A composition of matter comprising vanadium, non-water-contained hydrogen, phosphorus and non-water-contained oxygen, and having water of hydration, in accordance with the empirical formula:

$$VH_xPO_y \cdot uH_2O$$

wherein "x" has an average value in a range from about 1.29 to about 1.40, "y" has an average value in a range from about 5.47 to about 5.55, and "u" has an average value of at least about 0.01, at least a portion of said non-water contained oxygen present in a pyrophosphate group.

15. The composition of matter of claim 14 wherein "u" has an average value in a range from about 0.01 to about 2.0.

16. The composition of matter of claim 14 wherein said vanadium is present as vanadium of plus 4 valence and vanadium of plus 5 valence.

17. The composition of matter of claim 14 wherein said vanadium has an average valence in a range from about 4.64 to about 4.70.

18. A composition of matter having the structural formula:

$$(VO)_m(VO_2)_nH_{2n}(PO_4)_n(P_2O_7)_{m/2}$$

wherein m+n=3, "m" has an average value in a range from about 0.90 to about 1.07, and "n" has an average value in a range from about 1.93 to about 2.10.

19. The composition of matter of claim 19 further characterized by being substantially devoid of water and having a powder X-ray diffraction pattern, based on the copper K-shell transition spectrum, having major d-spacings of 4.30, 4.17 and 3.09 Å.

20. The composition of matter of claim 19 wherein said diffraction pattern is further characterized by said d-spacings having relative ratios of intensity as follow:

| d-spacing (Å) | Relative Intensity |
|---|---|
| 4.30 | 12 |
| 4.17 | 100 |
| 3.09 | 35 |

21. A composition of matter having the structural formula:

$$(VO)_m(VO_2)_nH_{2n}(PO_4)_n(P_2O_7)_{m/2} \cdot uH_2O$$

wherein m+n=3, "m" has an average value in a range from about 0.90 to about 1.07, "n" has an average value in a range from about 1.93 to about 2.10, and "u" has an average value of at least about 0.01.

22. The composition of matter of claim 21 wherein "u" has an average value in a range from about 0.01 to about 4.0.

23. The composition of matter of claim 21 further characterized by a powder X-ray diffraction pattern, based on the copper K-shell transition spectrum, having d-spacings of 7.17, 6.96, 3.04 and 2.37 Å.

24. The composition of matter of claim 23 wherein said diffraction pattern is further characterized by said d-spacings having relative ratios of intensity as follow:

| d-spacing (Å) | Relative Intensity |
|---|---|
| 7.17 | 100 |
| 6.96 | 12 |
| 3.04 | 25 |
| 2.37 | 5 |

* * * * *